United States Patent [19]
Crawford et al.

[11] Patent Number: 6,039,707
[45] Date of Patent: Mar. 21, 2000

[54] PELVIC SUPPORT AND WALKING ASSISTANCE DEVICE

[76] Inventors: Michael K. Crawford, 631 Knipp Rd., Houston, Tex. 77024; James M. Killian, 10215 Sugar Hill, Houston, Tex. 77042

[21] Appl. No.: 09/251,010

[22] Filed: Feb. 16, 1999

[51] Int. Cl.[7] .................................................. A61F 5/00
[52] U.S. Cl. ................................. 602/5; 602/18; 602/19
[58] Field of Search .................................... 128/869, 882; 602/16, 19, 23, 26

[56] References Cited

U.S. PATENT DOCUMENTS

| | | | |
|---|---|---|---|
| 4,531,515 | 7/1985 | Rolfes | 602/16 |
| 4,632,097 | 12/1986 | Brooks | 602/16 |
| 4,905,678 | 3/1990 | Cumins | 602/16 |
| 5,036,837 | 8/1991 | Mitchell et al. | |
| 5,358,469 | 10/1994 | Patchel et al. | |
| 5,602,412 | 4/1997 | Modglin | 602/16 |
| 5,658,241 | 8/1997 | Deharde et al. | |
| 5,662,595 | 9/1997 | Chesher et al. | |

*Primary Examiner*—Michael A. Brown
*Attorney, Agent, or Firm*—Gary L. Bush; Mayor, Day, Caldwell & Keeton L.L.P.

[57] ABSTRACT

A pelvic support and walking assistance device is disclosed which includes a trunk support member and a thigh lifting member coupled to each other at a pivot joint positioned opposite a hip joint of a user. The device functions to prevent pelvic sway. With a spring coupled with said pivot joint, the device further provides a thigh lifting torque to partially compensate for proximal leg weakness. The spring assistance pivot device includes a winding device that can be adjusted in use for varying forward torque for varying situations.

7 Claims, 6 Drawing Sheets

PELVIC SUPPORT AND WALKING ASSISTANCE DEVICE

BACKGROUND OF THE INVENTION

1. Field of the Invention

This invention relates generally to devices which aid humans in walking. In particular, the invention relates to a device which is designed to be strapped onto a person and which provides assistance in lifting the proximal leg (that is, the thigh) while taking a step. The invention also relates to a device to be worn by a person in order to stabilize lateral support muscles to assist in overcoming pelvic sway (called "hip drop") during walking.

2. Description of the Prior Art

Many neurological conditions cause muscle weakness of the proximal leg and pelvic instability. The proximal leg flexor muscles are situated between the knee and the pelvic bones and are attached to the knee and pelvic bones. Such proximal leg muscle weakness may exist even though the lower leg muscles below the knee are not weak. The condition of pelvic instability is recognized by an apparent unsteadiness of gait which is due to pelvic sway and lack of lateral support muscles. The neurological conditions which cause proximal leg muscle weakness and pelvic instability include brain lesions on the side opposite the weak leg and lesions in the spinal cord. Furthermore, lesions in the nerve roots, lumbar plexus and femoral nerve can result in proximal leg weakness and as a consequence, gait disorders.

The neurological conditions described above are often placed into one of the following disease categories:

(1) Multiple Sclerosis (MS) with spastic leg muscle weakness;
pelvic instability and gait unsteadiness;
(2) Stroke with spastic hemiparesis;
(3) Degenerative, traumatic and other spinal cord lesions; and
(4) Inflammatory, auto-immune and compressive lesions of the lumbar roots, lumbo-sacral plexus and femoral nerves.

The prior art has provided many braces designed for conditions known as foot drop and knee weakness, but devices have not been designed to aid a patient having proximal leg muscle weakness which is the primary factor resulting in gait instability. Examples of prior art leg braces follow.

U.S. Pat. No. 2,111,018 to Ahlar discloses a walking brace which includes a belt worn around a users waist and upper and lower leg braces which are strapped about a users leg.

U.S. Pat. No. 1,072,369 to Spahn discloses a knee and ankle brace with an upper portion fitted about the upper leg, a lower leg portion and a spring/lever arrangement connected between the upper and lower portions.

U.S. Pat. No. 5,054,476 to Petrofsky et al. discloses an orthosis for walking assistance, especially for people who have been paralyzed by a spinal cord injury. Upper leg braces are provided as a pair, one for each leg. Risers extend upwardly from the leg braces to a pelvic band. The risers are flexible. Hip joints couple the risers to the leg braces.

U.S. Pat. No. 5,743,837 to Dias et al discloses a body mounted device for exercising buttocks muscles. The device includes two hinge plates which are secured outwardly and to one side of respective hip joints of a user, where each of the hinge plates are provided with a pivot arm which pivots about the hinge plate. The pivot arm extends downwardly along the legs of the user, engaging the backs of he legs between the hip joints and knees. A resilient elastic band provides a forwardly directed biasing force on the back of the legs. During rearward pivoting of the legs, the muscles of the buttocks contract and are forced to overcome the biasing force exerted by the pivot arms on the legs of the user.

IDENTIFICATION OF OBJECTS OF THE INVENTION

A primary object of the invention is to provide a device which assists a user in lifting his or her leg when taking a step.

Another object of the invention is to provide a device which provides stabilization for lateral support muscles as an aid in overcoming pelvic sway or hip drop during walking.

Another object of the invention is to provide a device for aiding walking for a person with muscle weakness of the proximal leg with a spring providing lifting torque to the leg when taking a step and with a device for varying the spring lifting torque by the user.

SUMMARY OF THE INVENTION

The objects described above along, with other advantages and features of the invention, are incorporated in a device which provides pelvic support and walking assistance for a user with pelvic instability and/or muscle weakness of the proximal leg.

Stabilization of the pelvis results from a trunk support member which is strapped about the trunk of a user and which is coupled to a thigh linking member which is strapped about a thigh of the user. The trunk support member includes a lower lateral band which extends partially about the lower trunk of the user at a vertical position immediately above the hip bones and an upper lateral band which extends partially about the upper trunk of the user at a vertical position of the breast bone of the user. An upper connection plate is adjustably secured to the lower lateral band and to the upper lateral band. Alternatively, a single relatively thick strap may be fixed to an upper connection plate with a means for reasonably securing the strap about a user's lower abdomen.

The thigh linking member includes a thigh band strapped to the thigh of the user with a lower connection plate slidably coupled to the thigh strap. A pivot joint couples the lower connection plate to the upper connection plate. The pivot joint is placed to the side of the user's body at a position adjacent to the hip joint of the user. The trunk support member coupled by the pivot joint and the thigh linking member combine to provide necessary lateral support to prevent hip drop or pelvis sway of the user caused by weak hip muscles.

The device also includes a spiraled coiled spring placed at the pivot joint which provides forward upward torque to the lower connection plate and the thigh of the user with respect to the hip as the user begins a step with the lifting of his leg. The coiled spring assists hip flexion muscles by enhancing the lifting force of the thigh muscles when leg movement is initiated during walking. A manual adjustment device at the pivot joint allows the user to adjust the spring force and the upward torque.

BRIEF DESCRIPTION OF THE DRAWINGS

The objects, advantages, and features of the invention will become more apparent by reference to the drawings which are appended hereto and wherein like numerals indicate like parts and wherein an illustrative embodiment of the invention is shown, of which.

DETAILED DESCRIPTION OF THE PREFERRED EMBODIMENT OF THE INVENTION

Figure 1:
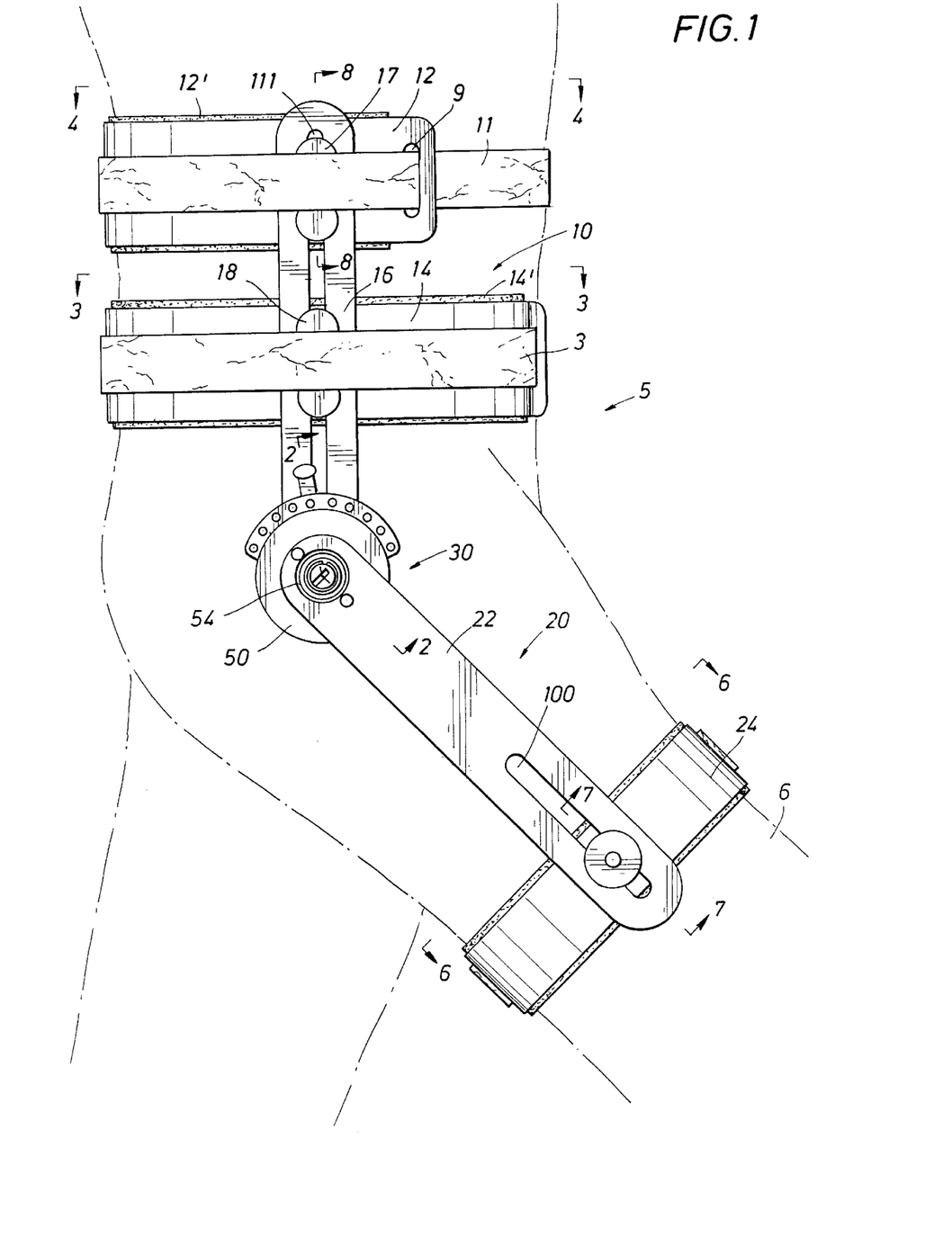
FIG. 1 is a side view of the device of the invention which shows trunk support member and a thigh linking member coupled to each other at a hip pivot joint.

FIG. 1 illustrates an embodiment of the invention in the pelvic support and walking assistance device 5 which includes a trunk support member shown generally at 10 and a thigh linking member 20 with pivot joint 30 which couples the two members 10, 20. The trunk support member 10 includes a lower lateral band 14 and an upper lateral band 12 each of which are adjustably secured to an upper connection plate 16. The lower lateral band 14 is arranged and designed to be secured about a user's torso at the waist area above the hip and pelvic bones of a user. The upper lateral band 12 is arranged and designed to be secured about a user's upper torso at a position slightly below the user's breast bone.

Figure 4:
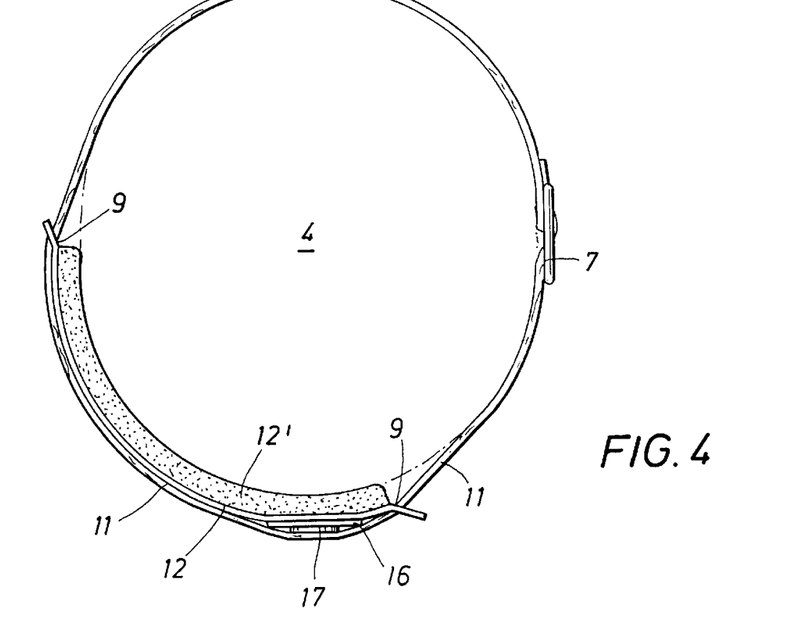
FIG. 4 is a downward view taken along lines 4—4 of FIG. 1 which illustrates the upper lateral band, which is removably secured about the upper torso of a user and adjustably secured to the upper connection plate.
Figure 8:
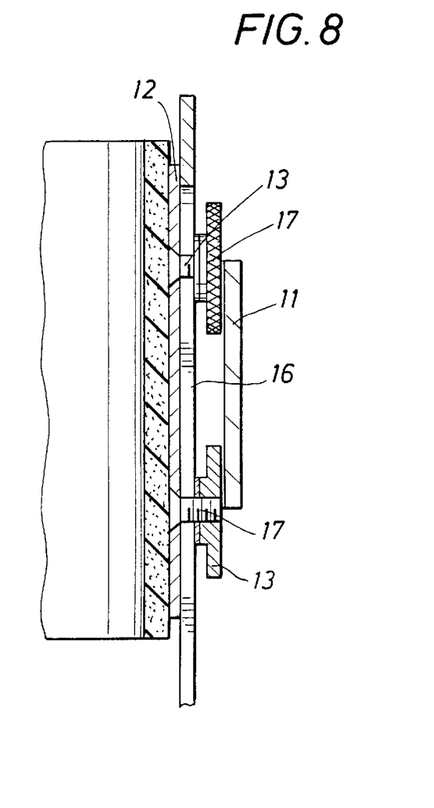
FIG. 8 is a view primarily in section taken along lines 8—8 of FIG. 1 which illustrates the adjustable connection between the upper lateral band and the upper connection plate.

As shown in FIGS. 1, 4 and 8 the upper lateral band 12 is vertically adjustably secured to upper connection plate 16 by means of thumb nuts 17 which may be tightened about threaded studs 13 fixed to upper lateral band 12. A slot 111 in upper connection plate 16 allows the upper lateral band 12 to be adjusted vertically, with the pivot joint 30 placed at the user's hip joint, so that the upper lateral band 12 can be placed about the user's torso at the breast bone position.

Figure 5:
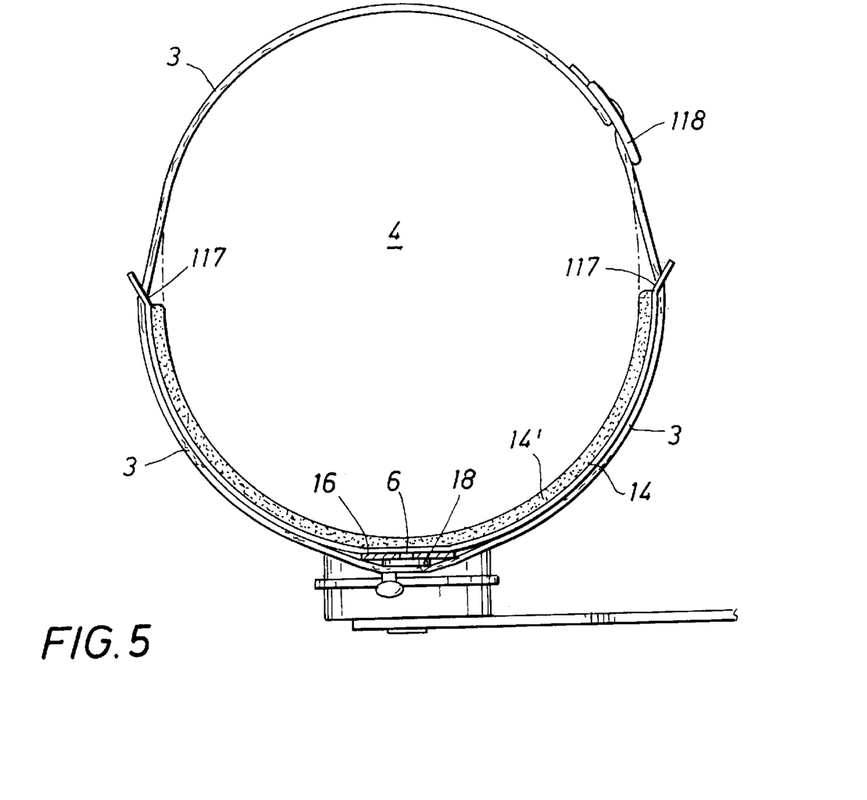
FIG. 5 is a downward view taken along lines 5—5 of FIG. 1 which illustrates the lower lateral band removably secured about the lower torso of a user.

In a similar way as shown in FIGS. 1 and 5, lower lateral band 14 may be adjusted vertically with respect to upper connection plate 16 by means of thumb nuts 18, which may be tightened about threaded studs 6 extending outwardly from lower lateral band 14.

As shown in FIGS. 1 and 4 the upper lateral band 12 extends in an arc of about ninety degrees about the upper torso 4 of the user. The band 12, formed of metal such as aluminum, has an inner soft foam cushion material 12' which bears against the torso 4 in use. A leather strap 11 extends about the outer side of band 12, through slots 9, and includes a buckle arrangement 7 for adjustable and removable securement of the upper lateral band 12 about the user's upper torso.

FIGS. 1 and 5 show the lower lateral band 14 which is constructed in a similar way to that of the upper lateral band 12. The lower lateral band 14 extends about 180 degrees around the lower torso 4 of the user. A leather strap 3 extends about lower lateral band 14 and through slots 117 at its ends. A buckle arrangement 118 is provided for adjustable and removable securement of the lower lateral band 14 about the lower abdomen of the user at a position above the hip bones of the user.

Figure 2:
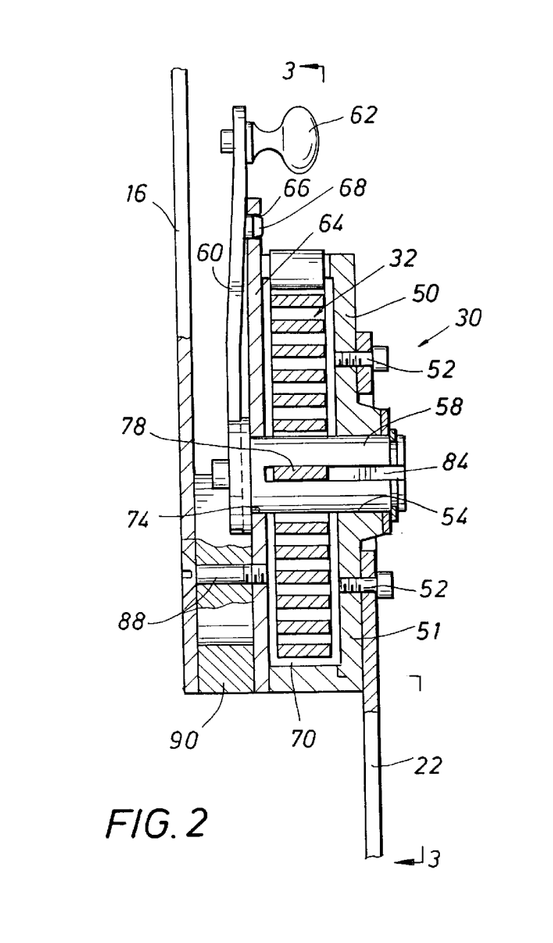
FIG. 2 is a sectional view along lines 2—2 of FIG. 1 which shows a coiled spring installed in the pivot joint between the upper connection plate of the trunk support member and a lower connection plate of the thigh linking member.

As shown in FIGS. 1 and 2 the pivot joint 30 is placed at the side of the hip area of the user at a position adjacent the hip joint of the user by adjusting the placement of upper connection plate 16 and the securement of the lower band 14 and upper band 12 to the user's torso 4.

The illustrations of FIGS. 1, 4 and 5 show that the lower lateral band 14 is placed in a semi-circle (i.e., with an angular arc of about 180°) with an attachment to the pivot joint 30 and the thigh linking member 20 at about mid-way in its angular length. In other words, lower lateral band 14 runs from a point mid-way of the front of the lower torso to a point mid-way of the back of the lower torso of the user. As shown especially in FIG. 4, the upper lateral band 12 is shorter in angular arc (i.e., with an angular arc of about 90°) and is connected to upper connection plate 16 at its front end and runs to a position further around the back of the user. As explained below, when in operation with the spring assist walking assistance mode of the thigh linking member, angular torque is transmitted from the lower connection plate 22 to the upper connection plate 16. The arrangement and design of the upper lateral band 12 and the lower lateral band 14, with the upper lateral band 12 being shorter in angular length than the lower lateral band 14 and covering more of the back of the user than does the lower lateral band 14, serve to react against such angular torque.

Figure 3:
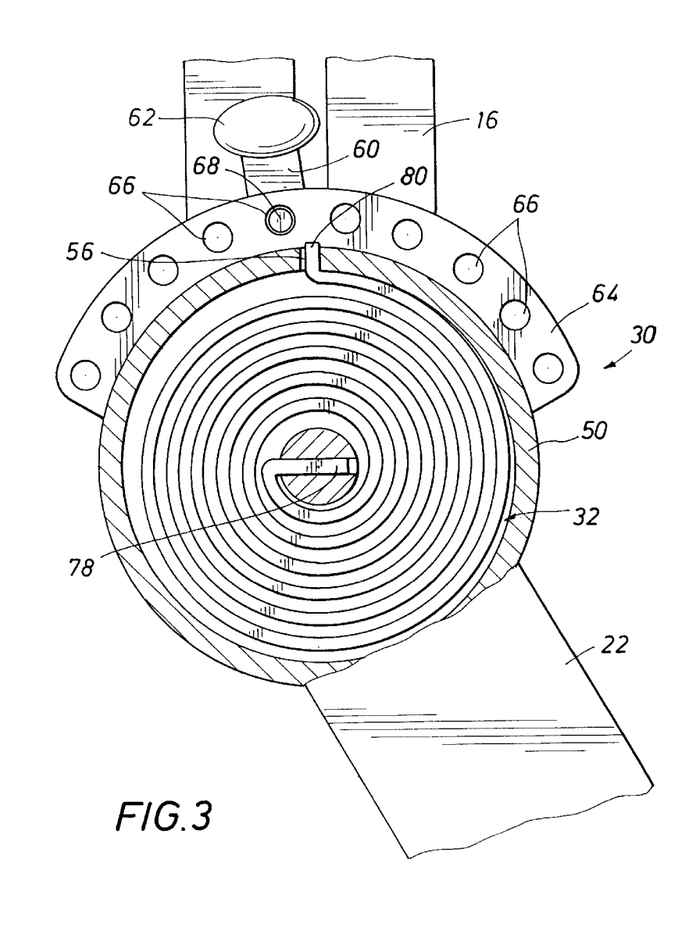
FIG. 3 is a view, partially in section taken along lines 3—3 of FIG. 2, showing the adjustable spring force arrangement of the device.

FIGS. 1, 2, and 3 illustrate the spring assist feature of the thigh linking member 20. It should be emphasized that the pelvic support function of the device 5 is accomplished with the arrangement of the trunk support member 10 and thigh linking member 20 coupled by means of pivot joint 30. Placement of a spiral coiled spring 32 in pivot joint 30 provides upward torque to the lower connection plate 22 and to the thigh lateral band 24 and ultimately to the thigh 6 of the user. Such upward torque assists the user in ling his thigh when taking a forward step.

The lower connection plate 22 is secured to a cylindrical housing 50 by means of fasteners such as threaded screws 52. The cylindrical housing 50 has a hole 54 bored into its outer end 51. The cylindrical housing provides an open ended cavity 70 in which is placed a spiral coiled spring 32. An adjustment arm 60, formed of spring steel, has a notched cylinder 58 at one end and a knob 62 and detent dog 68 at its other end. A detent plate 64 is provided with a hole 74 at its center and a plurality of detent holes 66 along an arc at a top extension of the plate 64. The adjustment arm and its notched cylinder 58 is assembled with the cylindrical housing 50 and the upper connection member 16 by placing the coiled spring 32 in the cavity 70 of the cylindrical housing. The coiled spring 32, formed of spring steel, has a key 78 formed at its inner end and a lip 80 found at its outer end. The notched cylinder 58 which is secured at about a ninety degree angle to the adjustment arm 60, is placed through hole 74 of detent plate 64 and through the center of coiled spring 32 such that the notch or key way 84 of the notched cylinder 58 has key 78 of spiral coiled spring 32 captured therein. The lip 80 of the coiled spring 32 is placed in a notch 56 of the cylindrical housing 50 as best shown in FIG. 3. The detent dog 68 of spring adjustment arm 60 is placed in one of the detent holes 74 of detent plate 64. The detent plate 64 is secured to the upper connection plate 16 by means of fasteners, such as threaded studs 88, through a spacer 90. The spacer 90 provides space for adjustment arm 60 to be moved in a space between the upper connection member 16 and the detent plate 64. The spacer 90 has a lower outer shape to match that of the bottom end of upper connection member 16 and the bottom end of detent plate 64 and cylindrical housing 50. The inner lower wall of the spacer 90 provides for threaded studs 88, yet is hollow so as not interfere with the operation of adjustment arm 60.

When assembled as described above and as illustrated in FIGS. 1, 2 and 3, the spiral coiled spring 32 is wound more tightly by shifting the adjustment arm 60 clockwise as viewed from FIG. 3 such that the detent dog 68 is placed in one of the detent holes 66 clockwise of the one illustrated in which detent dog 68 is placed. When the adjustment arm 60 is shifted counter-clockwise such that the detent dog 68 is placed in one of the detent holes 66 located counter-clockwise of the one illustrated in which the detent dog 68 is placed, the spring is relatively unwound thereby providing less torque to lower connection member 22 when the pivot joint 30 is positioned at the hip joint of the user of FIG. 1. As discussed above, the torque provided to the lower connection plate 22 by spring 32 of pivot joint 30 is reacted against by mean of the upper and lower bands 12, 14.

Figure 6:
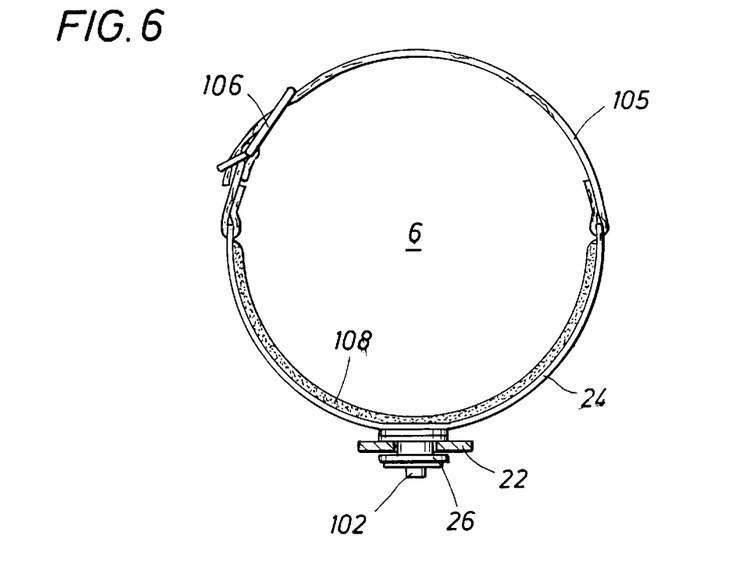
FIG. 6 is a downward view taken along lines 6—6 of FIG. 1 which illustrates a lateral band removably secured about the thigh of a user.
Figure 7:
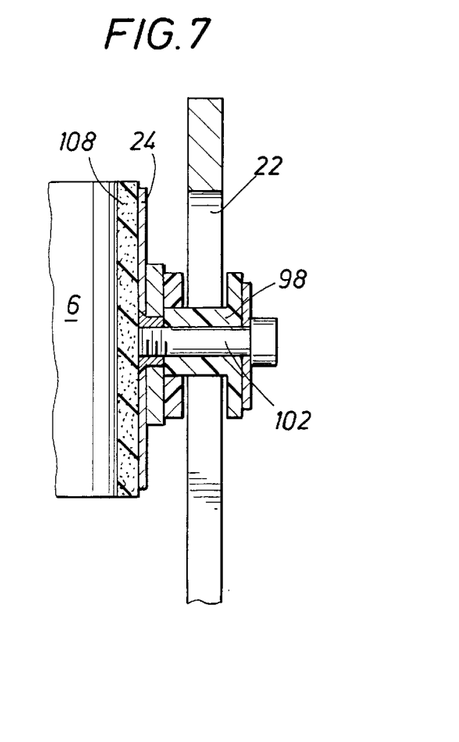
FIG. 7 is a sectional view taken along lines 7—7 of FIG. 1 which illustrates the sliding coupling of the thigh lateral band with the lower connection plate of the thigh linking member.

FIGS. 1 and 7 illustrate the arrangement of the thigh lateral band 24 and the coupling with the lower connection plate 22. A sliding member 98 is assembled in slot 100 of lower connection plate 22 so that relative movement between lower connection plate 22 and thigh lateral band 24 can occur when the thigh lateral band 24 is removably secured to the thigh 6 of the user. The sliding member 98 is secured to the thigh lateral band 24 by means of a fastener such as threaded stud 102. The thigh lateral band 24 is preferably secured to the thigh 6 of the user by means of a strap 105 and a buckle arrangement 106 as illustrated in FIG. 6. Padding material, such as a foam material 108 is secured to the inner surface of thigh lateral band 24 to protect the user from the force of the metallic band 24 being tightened and secured about thigh 6.

Figure 9:
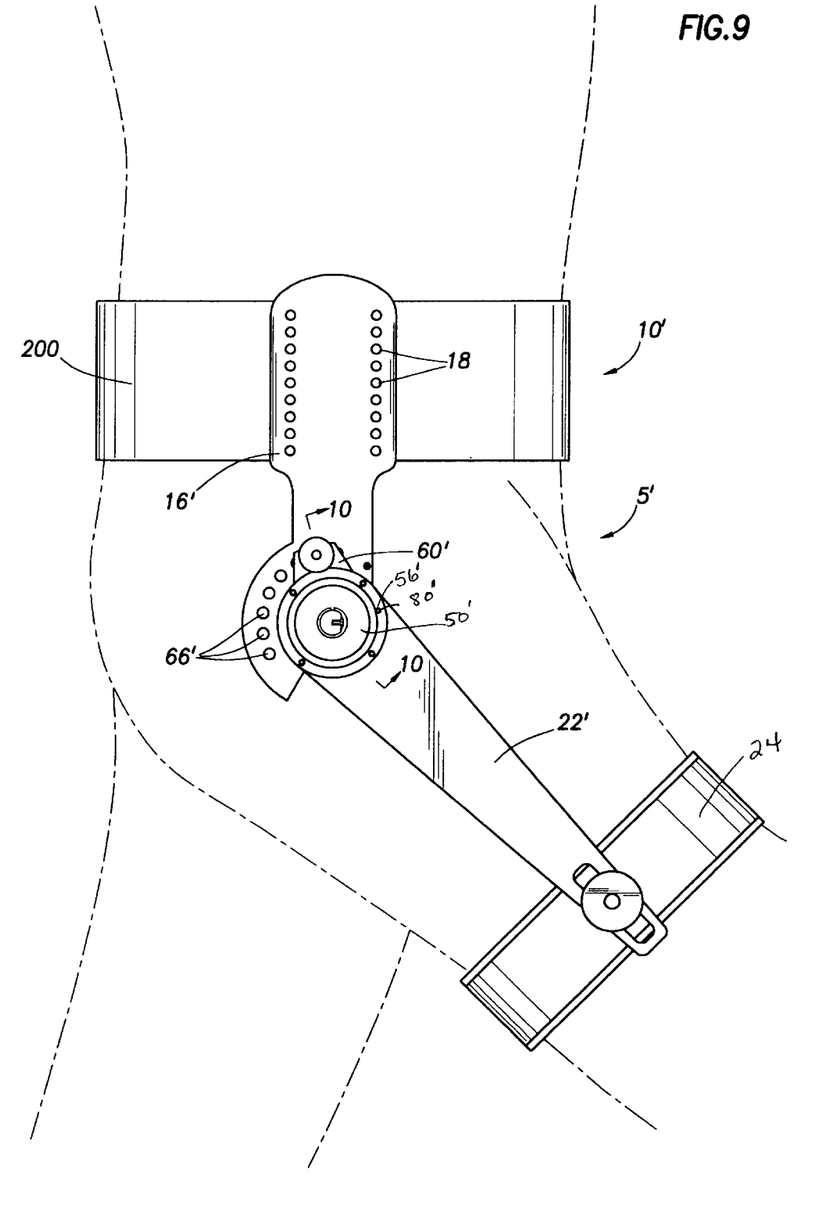
FIG. 9 is a side view of the device of the invention showing an alternative embodiment of the trunk support member and an alternative arrangement of a pivot joint of the device.
Figure 10:
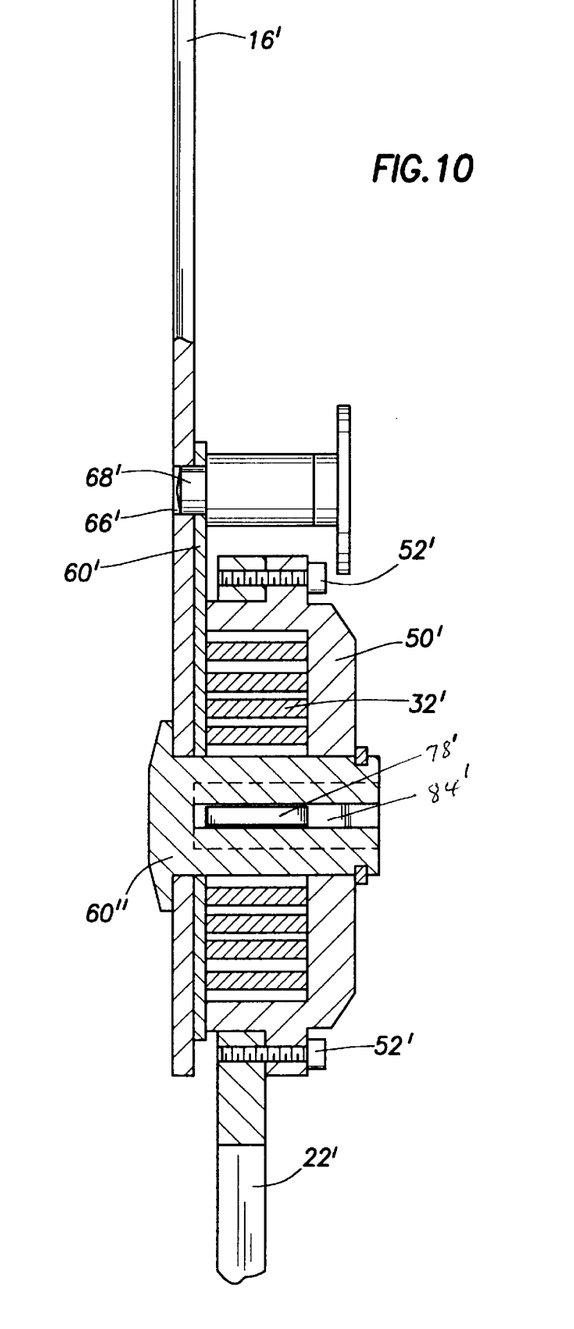
FIG. 10 is a sectional view along lines 10—10 of FIG. 9 which shows the alternative arrangement of a coiled spring installed in the pivot joint between the upper connection plate of the trunk support member and a lower connection plate of the thigh lining member.

FIGS. 9 and 10 illustrate an alternative embodiment 5 of the pelvic support and walking assistance device. A trunk support member 10' is provided in the form of a single thick strap 200 which is arranged and designed to be secured to the upper connection plate 16' by fasteners such as rivets 18. The strap 200 includes a buckle arrangement (not shown) for cinching the trunk support member 10 about the torso at a level slightly above the hip bones of the user.

As shown by FIGS. 9 and 10, the alternative embodiment 5 provides a spring winding and bearing member 60' which is placed between the lower end of the upper connection plate 16' and the cylindrical housing 50' for spring 32'. The spring 32' is adjustably captured between lower connection plate 22' and upper connection plate 16' by virtue of one end 78' being in a slot 84' of hub 60" (see FIG. 10) and the other end 80' being in a slot 56' of housing 50' (see FIG. 9). The bearing member 60' acts as a bearing surface between lower connection plate 22' and the upper connection plate 16'. The member 60' may be fabricated from brass or other rigid material characterized by a relatively low coefficient of friction. The hub 60" of member 60' extends through a hole in the upper connection plate 16'. Detent holes 66', arranged in an arc about a lower portion of upper connection plate 16' may be engaged by a dog 68' placed on the inner side of bearing member 60' so that the spring 32' may be wound tighter for more upward torque to the upper leg, or unwound for reducing the amount of upward torque. The cylindrical housing 50' for spring 32" is fixed to lower connection plate 22' by means of screws 52'.

The arrangement of FIGS. 9 and 10 is advantageous in that the lower connection plate 22' is adjacent the upper connection plate 16' rather than being radially offset therefrom as in FIGS. 1 and 2. Such alternative arrangement allows the pivot joint to be made more compact in size so that it does not extend far from a user's hip when it is strapped to a user.

In operation, a user positions the pelvic support and walling assistance device on his body, by locating the pivot joint 30 on the side of his hip area adjacent his hip joint. The upper lateral band 12 is vertically adjusted so as to be positioned at the breast bone area of the user and with the lower lateral band 14 at the lower abdomen a short distance above the hip bones. In the alternative embodiment of FIGS. 9 and 10, the trunk support member 10' in the form of a thick strap 200' is simply strapped about the lower abdomen of the user. The thigh lateral band 24 is positioned mid-way along the thigh 6 of the user and strapped thereto. If there is no spring in pivot joint 30, pelvic support provided by the device aids in the prevention of pelvic sway, because there is vertical support from the lower connection plate 22 through the pivot joint 30 to the upper connection plate 16. Such vertical support inhibits outward swaying of the hip, called hip drop, when the user walks.

With a coiled spring 32 in pivot joint 30, (or coiled spring 32' of FIGS. 9, 10) upward torque is applied to the thigh 6 of the user each time a step is taken. Weak proximal muscles are thereby augmented. The strong back leg muscles easily overcome the forward torque of the spring 32 (or spring 32') in returning the leg back to vertical position. The trunk support member 10 reacts against the torque of the lower connection plate.

The present invention and the best modes of practicing it have been described It is to be understood that the foregoing description is illustrative only and that other means and techniques can be employed without departing from the full scope of the invention as described in the appended claims.

What is claimed is:

1. A pelvic support and walking assistance device comprising, a trunk support member arranged and designed to be removably secured about a torso of a user, said trunk support member including an upper connection plate, a thigh linking member arranged and designed to be removably secured about a thigh of said user, said thigh support member including a lower connection plate, a pivot joint coupled to said upper connection plate and to said lower connection plate and arranged and designed for placement at a side of a hip of said user at a position opposite a hip joint of a user, and a resilient device coupled between said upper connection plate and said lower connection plate which applies forward torque to said lower connection plate when said user takes a step by raising said thigh, wherein said trunk support member applies a reactive torque from said torso of said user.

2. The pelvic support and walking assistance device of claim 1 wherein, said resilient device is a coiled spring mounted at said pivot joint, wherein one end of said spring is coupled to said upper connection plate, and the other end of said spring is coupled to said lower connection member.

3. The pelvic support and walking assistance device of claim 2 further comprising, a spring winding device which is coupled to said spring for winding or unwinding said spring, thereby respectively increasing or decreasing said forward torque applied to said thigh of a user when taking a forward step.

4. The pelvic support and walking assistance device of claim 3 further comprising, means for releasably locking said spring winding device at one of a plurality positions corresponding to different winding tensions applied to said spring.

5. The pelvic support device and walking assistance device of claim 2 wherein, said trunk support member includes a strap fixed to said upper connection plate.

6. The pelvic support and walking assistance device of claim 1 wherein, said trunk support member includes a lower lateral band which is arranged and designed for removable securement about the lower torso of said user and an upper lateral band which is arranged and designed for removable securement about the lower torso of said user.

7. The pelvic support and walking assistance device of claim 6 wherein, said thigh linking member includes a thigh lateral band which is arranged and designed to be removably secured about said thigh of said user, said thigh lateral band having a sliding member fixed thereto, said lower connection plate having an elongated slot in which said sliding member is positioned, whereby said lower connection plate is free to reciprocate about said sliding member when said thigh is raised or lowered from a vertical position.

* * * * *